US00PP27751P3

(12) United States Plant Patent
Suzuki

(10) Patent No.: US PP27,751 P3
(45) Date of Patent: Mar. 7, 2017

(54) ***LOROPETALUM* PLANT NAMED 'HAKUOU'**

(50) Latin Name: *Loropetalum chinense*
Varietal Denomination: HAKUOU

(71) Applicant: Yuji Suzuki, Kawaguchi (JP)

(72) Inventor: Yuji Suzuki, Kawaguchi (JP)

(73) Assignee: Spring Meadow Nursery, Inc, Grand Haven, MI (US)

( * ) Notice: Subject to any disclaimer, the term of this patent is extended or adjusted under 35 U.S.C. 154(b) by 83 days.

(21) Appl. No.: 14/544,871

(22) Filed: Feb. 26, 2015

(65) Prior Publication Data

US 2016/0262295 P1 Sep. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Loropetalum* cultivar named 'HAKUOU' is disclosed, characterized by dark green foliage and bright white re-blooming flowers. Plant form is dwarf, rounded, and dense. The new variety is a *Loropetalum*, normally produced as an outdoor garden or container plant.

2 Drawing Sheets

Figure 1:
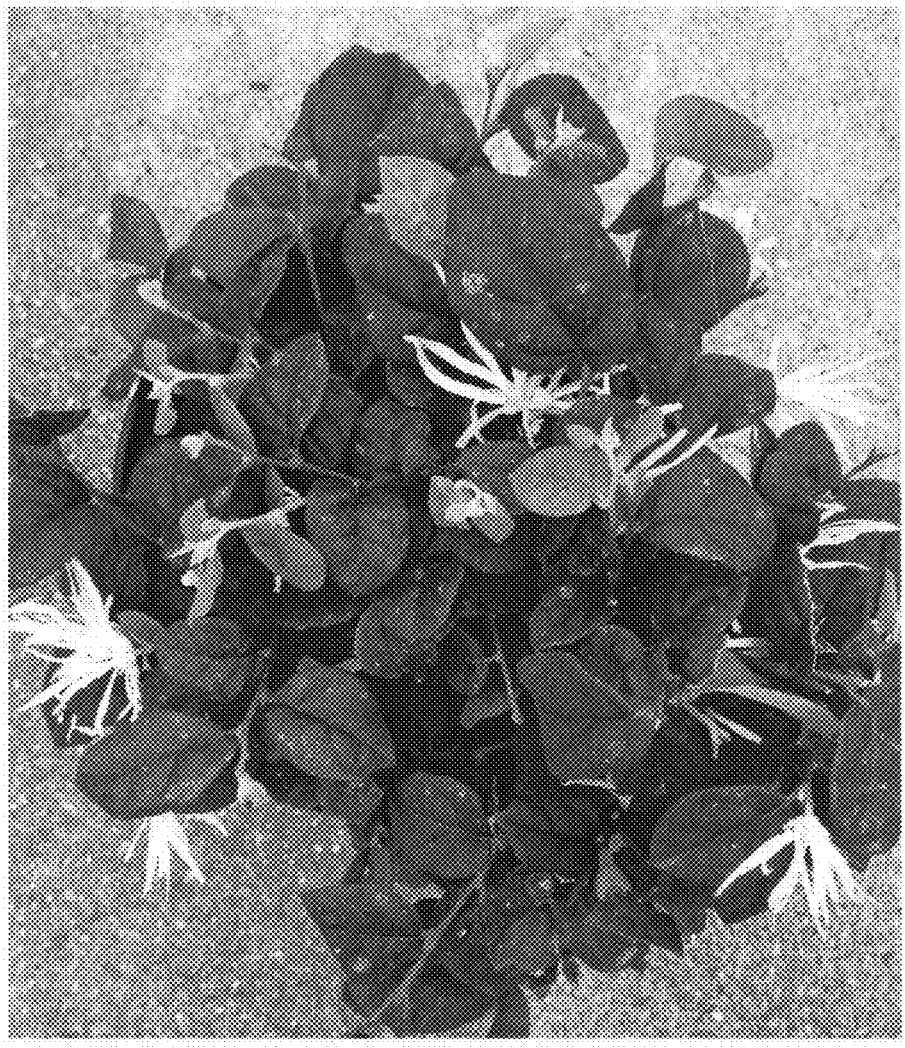

Latin name of the genus and species: *Loropetalum chinense*.

Variety denomination: 'HAKUOU'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with better foliage color and improved flowering for ornamental commercial applications. The cross resulting in this new variety was made during Apr. 20, 2005.

The seed parent is the, unpatented, propriety variety referred to as *Loropetalum* '5-7'. The pollen parent is the unpatented, propriety variety referred to as *Loropetalum* '5-64'. The new variety was discovered in a commercial nursery by the inventor in a group of seedlings resulting from the 2005 crossing, in Kawaguchi City, Saitama, Japan.

Asexual reproduction of the new cultivar was performed by softwood cuttings. This was first performed at a commercial nursery in Kawaguchi City, Saitama, Japan, in 2011 and has shown that the unique features of this cultivar are stable and reproduced true to type in 5 successive generations.

SUMMARY OF THE INVENTION

The cultivar 'HAKUOU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HAKUOU' These characteristics in combination distinguish 'HAKUOU' as a new and distinct *Loropetalum* cultivar:

1. Attractive dark green foliage with lighter green new growth.
2. Very attractive dense rounded habit.
3. Heavy re-blooming after initial Spring bloom.
4. Bright white flowers.
5. Shapely dwarf and dense habit (1-3' tall).

Plants of the new cultivar 'HAKUOU' are similar to plants of the seed parent, *Loropetalum* '5-7' in most horticultural characteristics, however, plants of the new cultivar 'HAKUOU' differs in the following;

1. Larger flowers.
2. Ovate foliage. The parent's foliage is more broad ovate.
3. Mounding growth habit. The parent's growth habit is spreading.
4. Dark green foliage, holds color well. The parent's foliage is dark green but can lighten.
5. Strong re-blooming. The parent variety is slightly re-blooming.

Plants of the new cultivar 'HAKUOU' are similar to plants of the pollen parent, *Loropetalum* '5-64' in most horticultural characteristics, however, plants of the new cultivar 'HAKUOU' differs in the following;

1. Larger flowers.
2. Mounding growth habit. The pollen parent growth habit is spreading.
3. Dark green foliage, holds color well. The parent's foliage is dark green but can lighten.
4. Strong re-blooming. The parent's is slightly re-blooming.

COMMERCIAL COMPARISON

Plants of the new cultivar 'HAKUOU' are comparable to the patented, commercial variety *Loropetalum* 'Shang-white' U.S. Plant Pat. No. 21,738. The two *Loropetalum* varieties are similar in most horticultural characteristics; however, the new variety 'HAKUOU' differs in the following:

1. Shorter habit, 1-3 feet tall. The comparator is 3-4 feet tall.

BRIEF DESCRIPTION OF THE PHOTOGRAPHS

The accompanying photograph in FIG. 1 illustrates in full color a typical plant of 'HAKUOU' grown in a 1 gallon pot. Age of the plant photographed is approximately 1 to 2 years old from a rooted cutting.

Figure 2:
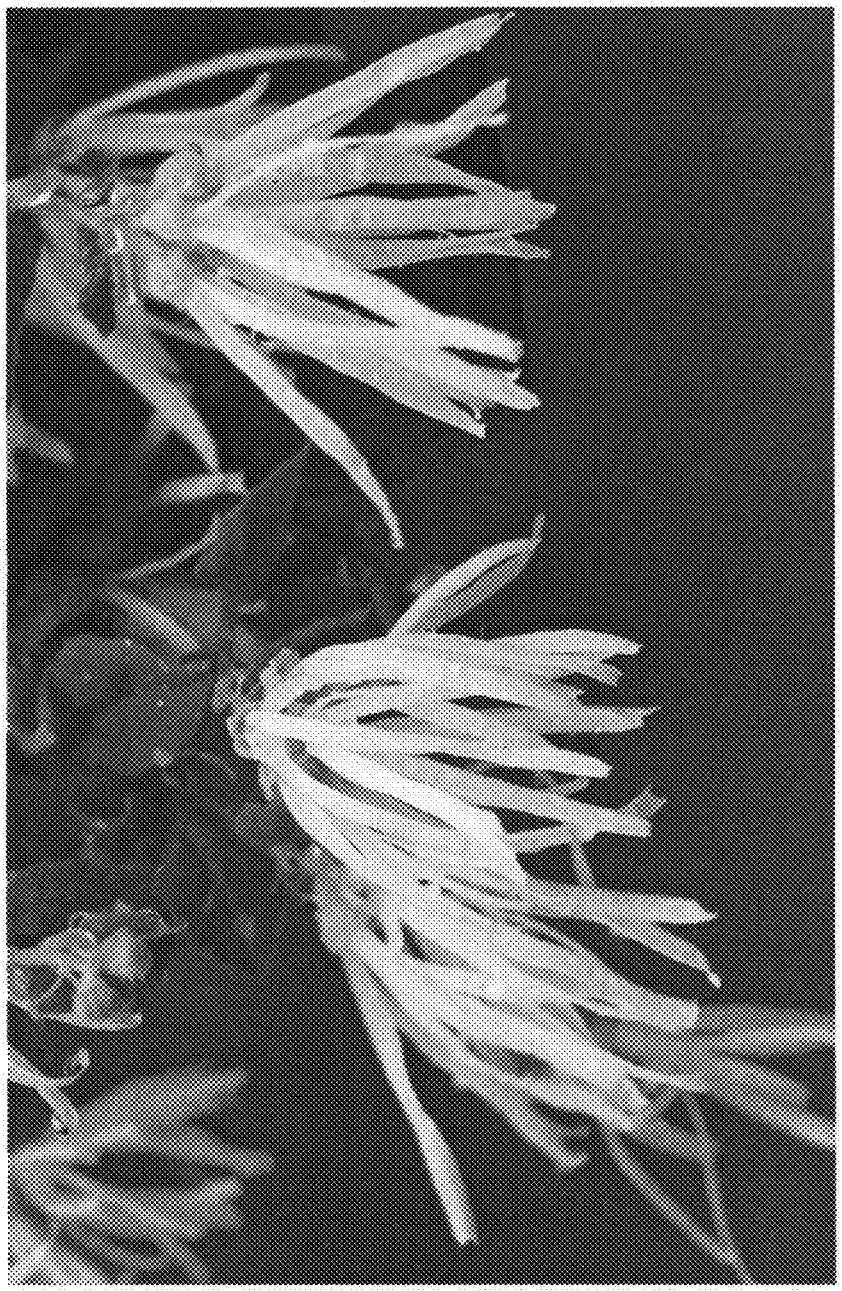

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HAKUOU' plants grown in a greenhouse, in Grand Haven Mich. The growing temperature averaged from 60-65° F. during the day and from 40-50° F. during the night. Growing conditions are double poly from Fall through Winter heated to 35° F. The poly was removed in the Spring. Measurements and numerical values represent averages of typical plant types.

Botanical classification: *Loropetalum* 'HAKUOU'.

PROPAGATION

Type of propagation typically used: Cutting.

Time to initiate roots: 18 days at 27° C.

Number of days to produce a rooted liner in summer: 110 days at 27° C.

Root description: Medium to thick, fibrous, free branching and fleshy. Roots are tan to white in color.

PLANT

Type of plant: Perennial shrub.

Age of plant described: Approximately 2 years old.

Container size of the plant described: 2 gallon.

Appropriate containers sizes: 1, 2 and 3 gallon nursery containers.

Growth habit: Rounded, mounded.

Height: 12-24 inches.

Plant spread: 36 inches.

Growth rate: Good.

Plant vigor: Good.

Branching characteristics: Lateral, some basal branching.

Pinching required: Yes.

Characteristics of primary lateral branches:

- *Length.*—20 cm.
- *Shape.*—Round.
- *Quantity.*—14 (in 1 gallon container).
- *Diameter.*—2.5 mm.
- *Color.*—Young stems: Near RHS Yellow-green 146B. Older stems: Near RHS Greyed-brown 199A.
- *Angle from center.*—0-15°.
- *Aspect.*—Straight.
- *Strength.*—Good.

Internode length: 1.5 cm.

Texture: Stem pubescence; more prevalent in younger stems.

FOLIAGE

Leaf:

- *Arrangement.*—Alternate, Single.
- *Quantity.*—Approximately 25 per branch.
- *Average length.*—2.75-5.5 cm.
- *Average width.*—1.5-4.0 cm.
- *Shape of blade.*—Ovate, rounded.
- *Tip.*—Acute.
- *Base.*—Oblique.
- *Margin.*—Entire.
- *Texture of top surface.*—Slightly rough due to sparse pubescence.
- *Texture of bottom surface.*—Ribbed due to protruding veins and coarse due to moderate pubescence.
- *Color.*—Young foliage upper side: Near RHS Yellow-green 146A with occasional overtones of Greyed-orange 164A. Young foliage under side: Glaucous. Near RHS Yellow-green 148A. Mature foliage upper side: Near RHS Green 139A. Mature foliage under side: Glaucous. Near RHS Yellow-green 147A.
- *Venation.*—Type: Pinnate. Venation color upper side: Midribs and veins are depressed on the upper side. Color does not differ from the leaf color. Venation color under side: Midribs and veins are prominent on the underside. Near RHS Yellow-green 145A.
- *Petiole.*—Length: 0.25 to 0.6 cm. Diameter: 1 mm. Color: Near RHS Yellow-green 146B.
- *Durability of foliage to stresses.*—Good.

FLOWER

Inflorescence and flower type and habit: Perfect flowers, comprised of strap-shaped petals, occurring in terminal (mainly) and axillary (occasionally) umbels.

Quantity of flowers per inflorescence: 3-7.

Flower type: Strap-shape, self-cleaning.

Flowering habit: Re-blooming.

Flower aspect: Upright and outward.

Quantity of flowers per lateral stem: 15-25.

Quantity of flowers per plant: 50 to 500, depending on maturity of plant.

Natural flowering season: Spring to Fall.

Fragrance: None.

Bud:

- *Shape.*—Obovate.
- *Length.*—4 mm.
- *Diameter.*—3 mm.
- *Color.*—Near RHS Yellow-green 145A.

Petals:

- *Quantity per flower.*—4.
- *Shape.*—Linear.
- *Margin.*—Entire.
- *Texture.*—Smooth, silky.
- *Appearance.*—Strap-shaped, un-fused.
- *Length.*—2.35 cm.
- *Width.*—2 mm.
- *Tip.*—Truncate.
- *Color.*—When opening: Upper surface: Near RHS White 155C. Lower surface: Near RHS White 155C. Fully opened: Upper surface: Near RHS White 155C. Lower surface: Near RHS White 155C. Petal color fading to: Near RHS Greyed-yellow 161B (only on tips).

Sepals:

*Quantity per flower.*—4.
*Appearance.*—Light green.
*Arrangement.*—Whorl.
*Shape.*—Ovate and fused, slightly curled outward.
*Length.*—4 mm.
*Width.*—3 mm.
*Tip.*—Slightly reflexed.
*Base.*—Fused.
*Margin.*—Entire, smooth.
*Color.*—Immature upper and lower side: Near RHS Yellow-green 145C. Mature upper and lower side: Near RHS Yellow-green 145C.

Calyx:

*Length.*—0.2 cm.
*Diameter.*—0.2 cm.

REPRODUCTIVE ORGANS

Stamens:

*Number.*—4.

Pistil:

*Number.*—2.

OTHER CHARACTERISTICS

Lowest temperature tolerant to: 5 to 10° F.

Disease/pest resistance: No unusual susceptibility to diseases or pests noted to date.

Fruits and seeds: Rarely observed. If produced, capsule size is approximately 1 cm long by 6 mm wide. Immature capsule colored near Yellow-Green 144A. Mature capsule colored Greyed-Brown 199B and N200B. Very few seeds observed within capsule.

Drought tolerance: Moderate to good drought tolerance once established.

What is claimed is:

1. A new and distinct cultivar of *Loropetalum* plant named 'HAKUOU' as herein illustrated and described.

* * * * *